(12) United States Patent
Wear et al.

(10) Patent No.: US 11,573,166 B2
(45) Date of Patent: Feb. 7, 2023

(54) SYSTEM AND METHOD FOR CALIBRATING A PARTICLE MONITORING SENSOR

(71) Applicant: Caterpillar Inc., Peoria, IL (US)

(72) Inventors: Daniel G. Wear, East Peoria, IL (US); Tom K. Shim, Edwards, IL (US)

(73) Assignee: Caterpillar Inc., Peoria, IL (US)

( * ) Notice: Subject to any disclaimer, the term of this patent is extended or adjusted under 35 U.S.C. 154(b) by 239 days.

(21) Appl. No.: 17/124,031

(22) Filed: Dec. 16, 2020

(65) Prior Publication Data

US 2022/0187186 A1 Jun. 16, 2022

(51) Int. Cl.
*G01N 15/14* (2006.01)
*G01N 33/28* (2006.01)
*G07C 5/08* (2006.01)

(52) U.S. Cl.
CPC ..... *G01N 15/1434* (2013.01); *G01N 33/2835* (2013.01); *G01N 2015/1486* (2013.01); *G07C 5/0808* (2013.01)

(58) Field of Classification Search
CPC ........... G01N 15/1434; G01N 15/0205; G01N 2015/1486; G01N 2015/0003; G01N 2015/0053
See application file for complete search history.

(56) References Cited

U.S. PATENT DOCUMENTS

| 7,082,758 | B2 | 8/2006 | Kageyama et al. |
| 8,852,875 | B2 | 10/2014 | Toner et al. |
| 2008/0008623 | A1 | 1/2008 | Reed |
| 2012/0140223 | A1 | 6/2012 | Mitchell |

(Continued)

FOREIGN PATENT DOCUMENTS

| CN | 108663292 A | 10/2018 |
| CN | 106644864 B | 2/2020 |

(Continued)

OTHER PUBLICATIONS

Written Opinion and International Search Report for Int'l. Patent Appln. No. PCT/US2021/063174, dated Feb. 24, 2022 (9 pgs).

*Primary Examiner* — Rebecca C Bryant
(74) *Attorney, Agent, or Firm* — Finnegan, Henderson, Farabow, Garrett & Dunner, LLP (57) ABSTRACT

A method for calibrating a contaminant detection device includes fluidly connecting the contaminant detection device in series to a test reservoir and a light-obscuration-type particle counter, pumping low-end, intermediate, and high-end test dust dilutions through the contaminant detection device and the particle counter until a particle count measured by the particle counter for each of the successive test dust dilutions stabilizes, and setting a low-end gain, an intermediate gain, and a high-end gain for the contaminant detection device based on the stabilized particle counts for each of the test dust dilutions using a first-sized test dust grade. A bubble counting gain of an aeration threshold for the device may be set according to a second test dust grade greater in size than the first-sized test dust grade, and associated with a voltage signal produced by the contaminate detection device indicative of the presence of an air bubble contained within the fluid during use of the fluid in heavy machinery.

20 Claims, 4 Drawing Sheets

(56) References Cited

U.S. PATENT DOCUMENTS

| | | | |
|---|---|---|---|
| 2016/0307726 A1 | 10/2016 | Hatakeyama | |
| 2017/0350878 A1 | 12/2017 | Holmes | |
| 2018/0003611 A1 | 1/2018 | Sells et al. | |
| 2019/0226947 A1* | 7/2019 | Young | G06N 20/10 |
| 2020/0070167 A1 | 3/2020 | Raillon | |
| 2020/0124516 A1 | 4/2020 | Vidal et al. | |
| 2020/0249143 A1 | 8/2020 | Takeuchi | |
| 2022/0187187 A1* | 6/2022 | Wear | G01N 33/2841 |

FOREIGN PATENT DOCUMENTS

| | | |
|---|---|---|
| EP | 3258241 | 12/2017 |
| EP | 3546955 | 12/2019 |

* cited by examiner

SYSTEM AND METHOD FOR CALIBRATING A PARTICLE MONITORING SENSOR

TECHNICAL FIELD

The present disclosure relates generally to a system and method for calibrating and utilizing the output from a particle monitoring sensor and, more particularly, to a system and method for calibrating and utilizing the output from a particle monitoring sensor monitoring fluid used in heavy machinery.

BACKGROUND

On-highway and off-highway heavy machinery typically comprise a plurality of components that cooperate to perform a variety of tasks. Failure of one or more components of a machine can often lead to a loss in some functionality of the machine, which may limit the performance capabilities of the machine. Some component failure events may be relatively minor and simple to detect and resolve, with no real collateral damage to other components of the machine. Other failure events, however, may be more serious, potentially damaging other components of the machine. For example, in hydraulic systems, a catastrophic pump failure may expel failure debris into the hydraulic fluid. This debris may be absorbed by one or more other components of the hydraulic system, potentially damaging these components. In addition, contaminates in hydraulic fluid such as particles and air bubbles may be an early warning of other potential problems such as the imminent failure of a filter or filter components, suction line leaks leading to a pump, operation of the machine on a slope or at a machine pose outside of acceptable operational parameters, low hydraulic fluid levels, or other machine component wear or failure.

While failure debris or contaminants may be prevented from circulating through the entire hydraulic system through the use of one or more hydraulic filters, the buildup of debris or contaminants may reduce the flow rate of the fluid. In hydraulic systems that deliver hydraulic fluid for performing tasks associated with the hydraulic system, the reduction in flow rate may prevent the requisite amount of fluid from reaching one or more critical components. Over time, these components may overheat, increasing the likelihood for premature wear and, eventually, failure of these components. Additionally, a prognostic of the remaining useful life of a filter and/or other machine components that interact with hydraulic fluids may be correlated to the presence of contaminants such as particles and air bubbles in the hydraulic fluids.

One method for identifying buildup of debris in hydraulic systems involves the use of a pressure differential switch that monitors the input and output pressure of a fluid filter. If the pressure differential exceeds a threshold value, the switch is triggered and a warning signal is generated notifying the machine operator that the filter may be clogged with debris, which may be indicative of a catastrophic failure of one or more components associated with the hydraulic system.

One problem with threshold-based failure detection circuits is that, because component failure often manifests itself very quickly, the pressure differential may not be large enough to trigger the alarm until after the failure event has occurred. Such late detection of failure events may potentially cause damage to other components in the fluid channel, as contaminate particles that may have been expelled by the failed component may cause damage to components located between the failed component and the fluid filter. These particles may be difficult to remove once introduced to the system, and in addition to causing catastrophic component failure to one or more components in the short-term, may lead to long-term contingent component wear as these residual particles may remain in the system indefinitely.

Furthermore, late detection of failure events for certain "critical" components such as, for example, a hydraulic pump used to drive the tracks of a machine, may dramatically decrease worksite productivity. For example, if the failure event immobilizes or otherwise disables the machine, performance of tasks that depend upon the operation of the machine may be delayed. In addition, if the machine breaks down while operating in the worksite, the machine may present an obstacle to other machines. Thus, in order to limit the effects of catastrophic component failure and/or contingent component failure on the operations of a machine and worksite, a system for early detection of trends such as an increase in the contaminant levels in hydraulic fluids that may lead to machine component failure may be beneficial.

At least one system has been developed for predicting a remaining lifespan of a hydraulic pump. For example, U.S. Pat. No. 7,082,758 ("the '758 patent) to Kageyama et al. describes a system for monitoring long-term and short-term trends associated with pressure differential data measured across a hydraulic filter. The system may predict a pump failure or estimate a pump lifespan based on the degree of deviation between the long-term trend data and the short-term trend data.

Although the system of '758 patent may be effective in predicting component failure in certain situations, the system of the '758 patent may have several disadvantages. For example, differential pressure across the pump filter will typically only begin increasing after the filter chamber has filled, which may not occur until after significant failure contaminates such as particles or air bubbles have already been introduced into the fluid. Consequently, by the time the system of the '758 patent detects an upward trend in the differential pressure across the filter or the presence of unacceptable aeration levels, one or more components may have already sustained significant damage. Moreover, the system of the '758 patent does not provide any means for distinguishing between contaminants such as particles and air bubbles in hydraulic fluid, or compensating for aeration levels in hydraulic fluid used in heavy machinery when identifying levels of solid contaminant particles and prognosticating life expectancy of filters and other components associated with the hydraulic fluid.

The presently disclosed systems and methods for calibrating and utilizing the output from a particle monitoring sensor monitoring fluid used in heavy machinery are directed toward overcoming one or more of the problems set forth above.

SUMMARY

In accordance with one aspect, the present disclosure is directed toward a method for calibrating a contaminant detection device configured to determine a level of contamination in a fluid using an analog integrator that sums areas of shadows cast by contaminants in a fluid passing through a passageway when a light emitting diode (LED) is used to illuminate the fluid and a photodiode is used to generate a voltage signal indicative of the area of each shadow, with the analog integrator integrating the resultant voltage signals over time. The method may include fluidly connecting one or more of the contaminant detection devices in series to a test reservoir and to a light-obscuration-type particle counter, preparing a low-end test dust dilution of a first-sized test dust grade mixed with the fluid to create a first test dust mass-per-volume of the fluid, preparing an intermediate test dust dilution of the first-sized test dust grade mixed with the fluid to create a second test dust mass-per-volume of the fluid, the second test dust mass-per-volume being greater than the first test dust mass-per-volume, preparing a high-end test dust dilution of the first-sized test dust grade mixed with the fluid to create a third test dust mass-per-volume of the fluid, the third test dust mass-per-volume being greater than the second test dust mass-per-volume, successively pouring each of the low-end, intermediate, and high-end test dust dilutions into the test reservoir, and pumping each of the test dust dilutions through each of the one or more contaminant detection devices and the particle counter until a particle count measured by the particle counter for each of the successive test dust dilutions stabilizes. The method may further include setting a low-end gain, an intermediate gain, and a high-end gain for each of the one or more contaminant detection devices based on the stabilized particle counts for each of the test dust dilutions using the first-sized test dust grade. The method may still further include preparing an aeration bubble counter test dust dilution of a second-sized test dust grade greater in size than the first-sized test dust grade and mixed with the fluid, wherein the second-sized test dust grade comprises at least 90% of its volume containing dust particles falling within a range of sizes larger than a predetermined cut-off particle size associated with a voltage signal produced by one of the one or more contaminate detection devices and indicative of the presence of an air bubble contained within the fluid during use of the fluid in heavy machinery, pouring the aeration bubble counter test dust dilution into the test reservoir and pumping the aeration bubble counter test dust dilution through each of the one or more contaminant detection devices and the particle counter until a particle count measured by the particle counter for the aeration bubble counter test dust dilutions stabilizes, and setting a bubble counting gain of an aeration threshold for each of the one or more contaminant detection devices such that each of the devices rejects approximately 70-80% or more of the voltage signals generated as a result of the aeration bubble counter test dust dilution being pumped through the device.

According to another aspect, the present disclosure is directed toward a system configured for calibrating a contaminant detection device, wherein the contaminant detection device determines a level of contamination in a fluid using an analog integrator that sums areas of shadows cast by contaminants in a fluid passing through a passageway when a light emitting diode (LED) illuminates the fluid as it passes through the passageway, and a photodiode generates a voltage signal indicative of the area of each shadow, with the analog integrator integrating the resultant voltage signals over time. The system may include a test reservoir, a light-obscuration-type particle counter, one or more of the contaminant detection devices fluidly connected in series to the test reservoir and the light-obscuration-type particle counter, a low-end test dust dilution prepared from a first-sized test dust grade mixed with the fluid to create a first test dust mass-per-volume of the fluid, an intermediate test dust dilution prepared from the first-sized test dust grade mixed with the fluid to create a second test dust mass-per-volume of the fluid, the second test dust mass-per-volume being greater than the first test dust mass-per-volume, and a high-end test dust dilution prepared from the first-sized test dust grade mixed with the fluid to create a third test dust mass-per-volume of the fluid, the third test dust mass-per-volume being greater than the second test dust mass-per-volume. The system may also include a pump configured to successively pump each of the low-end, intermediate, and high-end test dust dilutions from the test reservoir through each of the one or more contaminant detection devices and the particle counter until a particle count measured by the particle counter for each of the successive test dust dilutions stabilizes, a first input mechanism for setting a low-end gain, an intermediate gain, and a high-end gain for each of the one or more contaminant detection devices based on the stabilized particle counts for each of the test dust dilutions using the first-sized test dust grade, and an aeration bubble counter test dust dilution prepared from a second-sized test dust grade greater in size than the first-sized test dust grade and mixed with the fluid, wherein the second-sized test dust grade comprises at least 90% of its volume containing dust particles falling within a range of sizes larger than a cut-off size associated with a voltage signal produced by one of the one or more contaminate detection devices indicative of the presence of an air bubble contained within the fluid during use of the fluid in heavy machinery. The pump may also be configured to pump the aeration bubble counter test dust dilution from the test reservoir through each of the one or more contaminant detection devices and the particle counter until a particle count measured by the particle counter for the aeration bubble counter test dust dilutions stabilizes. A second input mechanism may be configured for setting a bubble counting gain for each of the one or more contaminant detection devices such that each of the devices rejects approximately 70-80% or more of the voltage signals generated as a result of the aeration bubble counter test dust dilution being pumped through the device.

In accordance with another aspect, the present disclosure is directed toward a system for early detection of potential operational issues on heavy machinery. The system may include a hydraulic fluid contaminant detection device, wherein the contaminant detection device determines a level of contamination in a hydraulic fluid used in the heavy machinery by using an analog integrator that sums areas of shadows cast by contaminants in the hydraulic fluid passing through a passageway when a light emitting diode (LED) illuminates the hydraulic fluid as it passes through the passageway, and a photodiode generates a voltage signal indicative of the area of each shadow, with the analog integrator integrating the resultant voltage signals over time. The system may include a test reservoir fluidly connected to the hydraulic fluid contamination detection device, a light-obscuration-type particle counter fluidly connected downstream of the hydraulic fluid contamination detection device, a low-end test dust dilution prepared from a first-sized test dust grade mixed with the hydraulic fluid to create a first test dust mass-per-volume of the hydraulic fluid, an intermediate test dust dilution prepared from the first-sized test dust grade mixed with the hydraulic fluid to create a second test dust mass-per-volume of the hydraulic fluid, the second test dust mass-per-volume being greater than the first test dust mass-per-volume, and a high-end test dust dilution prepared from the first-sized test dust grade mixed with the hydraulic fluid to create a third test dust mass-per-volume of the hydraulic fluid, the third test dust mass-per-volume being greater than the second test dust mass-per-volume. The system may further include a pump configured to successively pump each of the low-end, intermediate, and high-end test dust dilutions from the test reservoir through the hydraulic fluid contaminant detection device and the particle counter until a particle count measured by the particle counter for each of the successive test dust dilutions stabilizes, a first input mechanism for setting a low-end gain, an intermediate gain, and a high-end gain for the hydraulic fluid contaminant detection device based on the stabilized particle counts for each of the test dust dilutions using the first-sized test dust grade, and an aeration bubble counter test dust dilution prepared from a second-sized test dust grade greater in size than the first-sized test dust grade and mixed with the hydraulic fluid, wherein the second-sized test dust grade comprises at least 90% of its volume containing dust particles falling within a range of sizes larger than a cut-off size associated with a voltage signal produced by the hydraulic fluid contaminate detection device indicative of the presence of an air bubble contained within the hydraulic fluid during use of the hydraulic fluid in the heavy machinery. The pump may be further configured to pump the aeration bubble counter test dust dilution from the test reservoir through the hydraulic fluid contaminant detection device and the particle counter until a particle count measured by the particle counter for the aeration bubble counter test dust dilution stabilizes, and the system may further include a second input mechanism for setting a bubble counting gain for the hydraulic fluid contaminant detection device such that the device rejects approximately 70-80% or more of the voltage signals generated as a result of the aeration bubble counter test dust dilution being pumped through the device.

DETAILED DESCRIPTION

Figure 1:
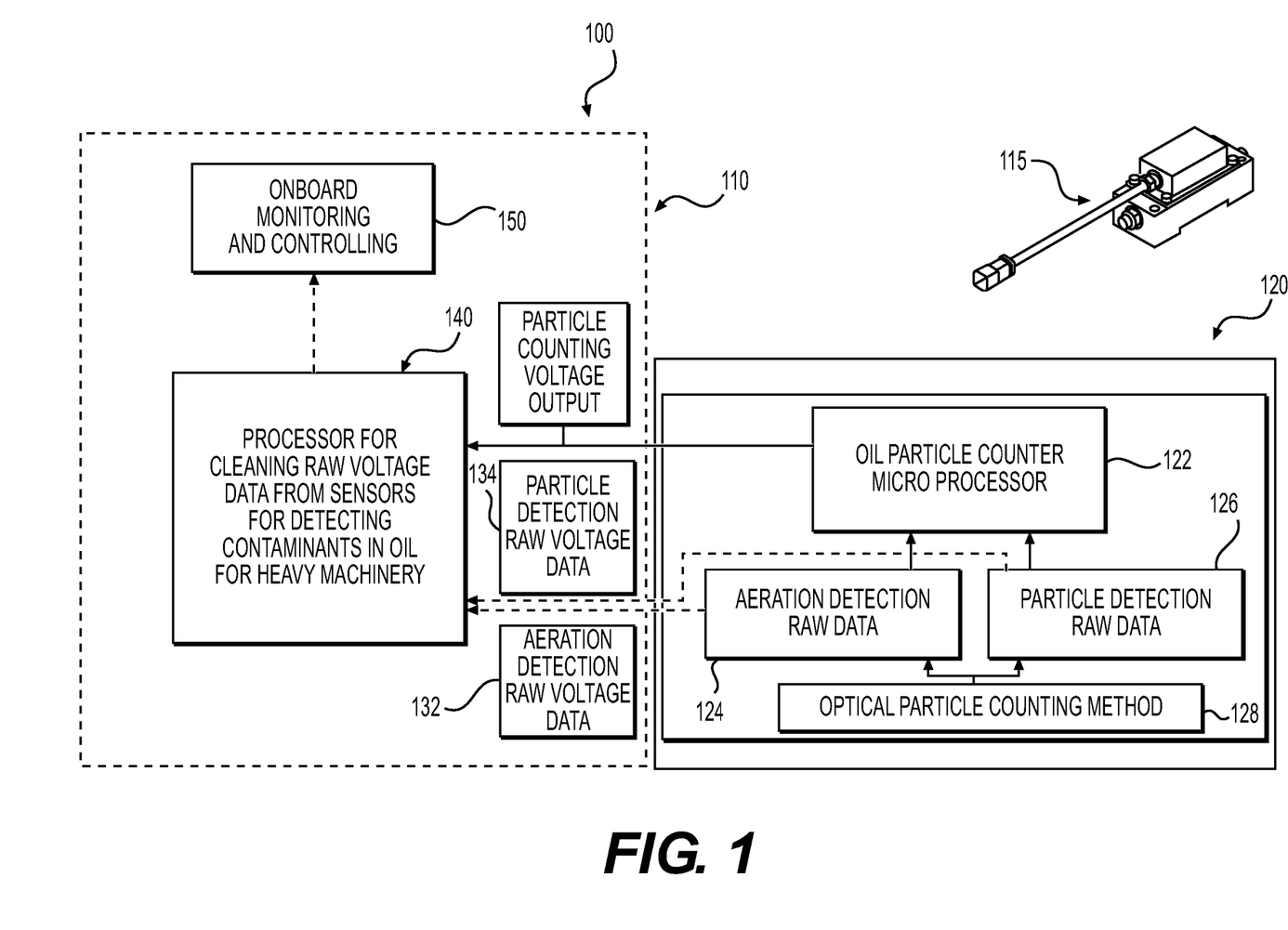
FIG. 1 illustrates a schematic of an exemplary system for utilizing raw voltage signals indicative of particle contaminants and an aeration level in a fluid passing through an optical particle sensor.

FIG. 1 illustrates an exemplary machine system 100 for utilizing raw voltage signals generated by an exemplary optical particle sensor 115 indicative of particle contaminants and air bubbles or an aeration level in a fluid passing through the optical particle sensor. Exemplary optical particle sensor 115 may include an internal control system 120 characterized by an oil particle counter microprocessor 122 configured to receive aeration detection raw voltage data 124 indicative of the number of air bubbles or quantity of aeration detected in a fluid being tested, and particle detection raw voltage data 126 indicative of the number of solid contaminate particles detected during implementation of an optical particle counting method 128. As shown in FIG. 1, optical particle sensor 115 may be configured to process raw voltage data 124, 126 internally using oil particle counter microprocessor 122, and produce a particle counting voltage output suitable for some applications.

A light emitting section of optical particle sensor 115, which may include one or more light emitting diodes (LEDs), which may be configured to continuously emit light into a fluid passing through a passageway in the sensor, and a light receiving section including one or more photodiodes may be configured to continuously receive the light that is continuously emitted from the light emitting section and that has passed through the fluid. The light receiving section may be configured to convert the continuously received light into a continuous electrical signal that includes the aeration detection raw voltage data 124, indicative of the number of air bubbles or level of aeration in the fluid, and the particle detection raw voltage data 126, indicative of the number and size of solid contaminate particles in the fluid. The one or more photodiodes of the light receiving section may be configured to produce differing amounts of voltage depending on the areas of shadows cast on the photodiodes by solid contaminate particles and air bubbles in the fluid passing through the passageway of the sensor. Oil particle counter microprocessor 122 of optical particle sensor 115 may include one or more algorithms designed to compensate for errors in measurements of the amount of solid contaminant particles in the fluid that may be caused by an excessive amount of air bubbles or aeration in the fluid. Such algorithms may include amplifying voltage signals produced by the one or more photodiodes and affected by shadows cast on the photodiodes by air bubbles and solid contaminate particles. The voltage signals indicative of air bubbles may be amplified by an amplification ratio that is less than an amplification ratio applied to voltage signals indicative of solid contaminant particles in the fluid, thereby reducing the effects on particle counts caused by the air bubbles or excessive aeration in the fluid. Additionally and/or alternatively, an algorithm implemented by oil particle counter microprocessor 122 may use voltage signals generated immediately before the voltage signals that are generated by air bubbles or aeration above a threshold area in the fluid, ignoring the voltage signals generated by air bubbles above the threshold area, thereby also reducing the effects caused by the air bubbles. However, as air bubbles become more prevalent in the fluid, creating an area of shadows on the photodiodes above a certain threshold, and the aeration detection raw voltage data increases, the ability of the oil particle counter microprocessor 122 to compensate for potential errors in the voltage signals and particle count may be limited.

To avoid errors in solid contaminate particle counts that may result when using optical particle sensor 115 for determining the amount of contaminants in fluids such as hydraulic fluids used in heavy machinery, which may be susceptible to high levels of aeration and air bubbles, an exemplary embodiment according to this disclosure may include receiving an aeration detection raw voltage data output 132 and a particle detection raw voltage data output 134 from control system 120 of optical particle sensor 115 at an external data processing system 110 separate and independent from optical particle sensor 115. In various embodiments according to this disclosure, terminals or other connectors may be provided on optical particle sensor 115, enabling external data processing system 110 to obtain raw voltage data produced by photodiodes in the sensor as the raw voltage data changes according to the amount of solid contaminate particles and air bubbles contained in a fluid being tested by the sensor.

External data processing system 110 may be located onboard equipment that benefits from real time monitoring of contaminates present in fluids used by the equipment. Alternatively, output from external data processing system 110 may be provided to equipment such as heavy machinery operating at various work sites over wired, wireless, or cellular networks. Whether located onboard machinery or offboard and communicatively coupled to the machinery, external data processing system 110 may be configured to receive the raw voltage data from one or more photodiodes contained within optical particle sensor 115. The photodiodes may be configured to generate voltage signals correlated to the area of shadows cast on the photodiodes as light from a light emitting diode (LED) within optical particle sensor 115 illuminates a fluid being tested as it passes through a passageway of the sensor. The passageway may be a translucent or transparent medium through which the fluid being tested is pumped, with the LED shining light through the passageway and onto the photodiodes positioned on an opposite side of the passageway from the LED. Solid contaminate particles and air bubbles in the fluid may result in shadows of different sizes and cumulative areas being cast on the photodiodes, thus affecting the amount of voltage produced by the photodiodes. An analog integrator may be provided to sum the areas of the shadows cast by contaminants in the fluid passing through the passageway of optical particle sensor 115 when a light emitting diode (LED) illuminates the fluid as it passes through the passageway, and integrate the resultant voltage signals over time to produce the raw voltage data outputs 132, 134.

As shown in FIG. 1, external data processing system 110 may include one or more processors such as processor 140 configured to analyze and clean the separate raw voltage data outputs retrieved from optical particle sensor 115. The raw voltage data outputs may be accessible through electrical terminals or other connectors provided on optical particle sensor 115 and electrically connected to receive voltage outputs from photodiodes of optical particle sensor 115 configured to generate aeration detection raw voltage data 132 and particle detection raw voltage data 134. The one or more processors 140 of external data processing system 110 may receive the raw voltage data from optical particle sensor 115, analyze the data, and determine when the presence of air bubbles or aeration in the fluid has exceeded a threshold level beyond which the accuracy of particle detection raw voltage 134 is likely to be so degraded that it should be ignored.

Outputs from the one or more processors 140 of external data processing system 110 may be provided to an onboard monitoring and controlling module 150 of machine system 100 on heavy machinery or other equipment that benefits from real time information on the amount of contaminates in fluids used by the equipment. The equipment may include one or more components that perform individual tasks that contribute to a machine environment task, such as mining, construction, transportation, agriculture, manufacturing, or any other type of task associated with other types of industries. In some implementations, onboard monitoring and controlling module 150 may be mounted on one or more machines communicatively coupled to a condition monitoring system via one or more communication networks. Onboard monitoring and controlling module 150 may be configured to monitor, collect, control, and/or filter information associated with the levels of contaminates in fluids used during operation of one or more machines, and if desired, may be configured to also distribute the information to one or more back-end systems, such as a central condition monitoring system in a back office or central command center, and/or systems available to subscribers such as customers and operators of the machines.

Figure 2:
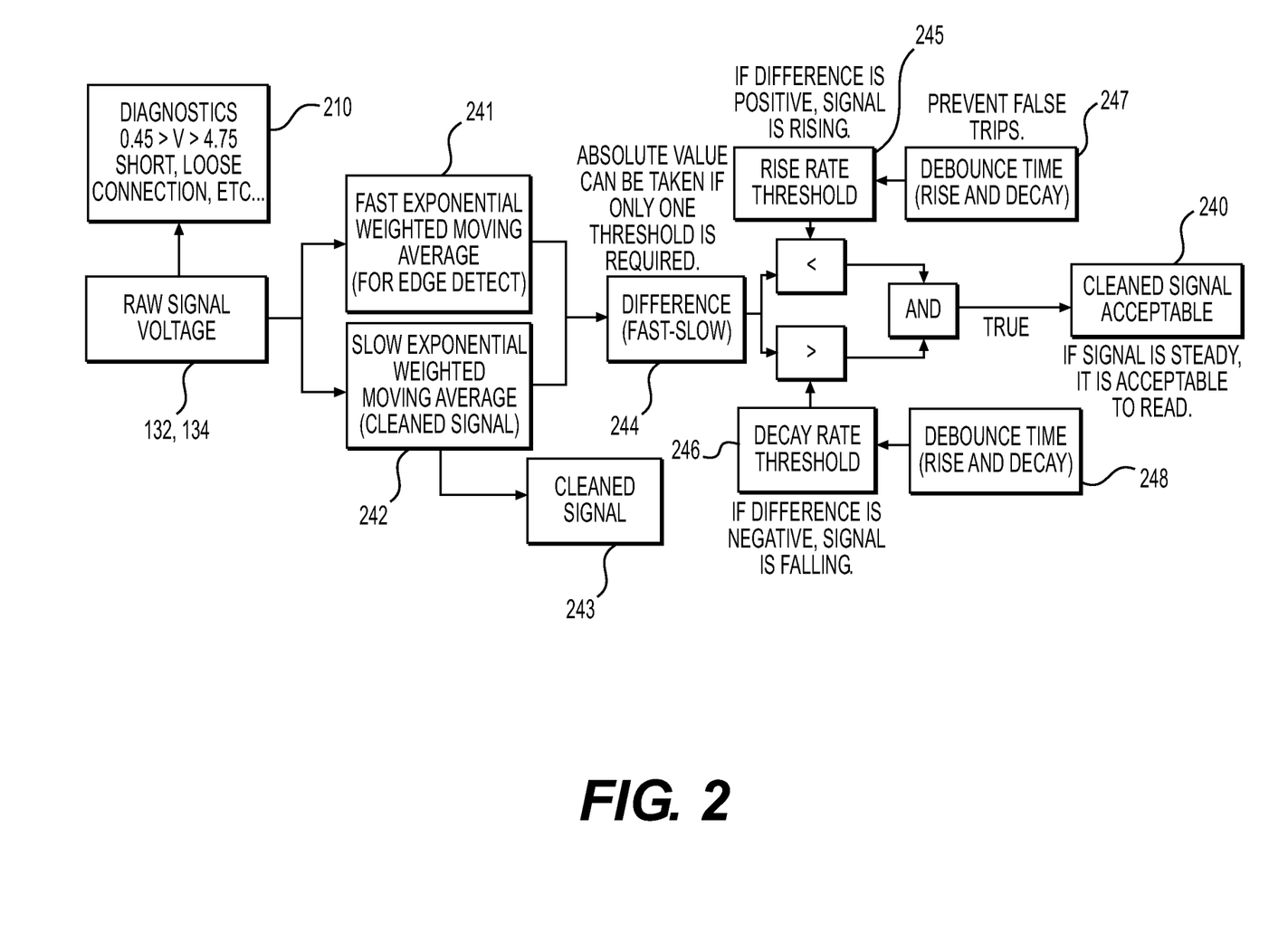
FIG. 2 illustrates an exemplary method for processing the raw voltage signals output by the optical particle sensor of the exemplary system shown in FIG. 1.
Figure 3:
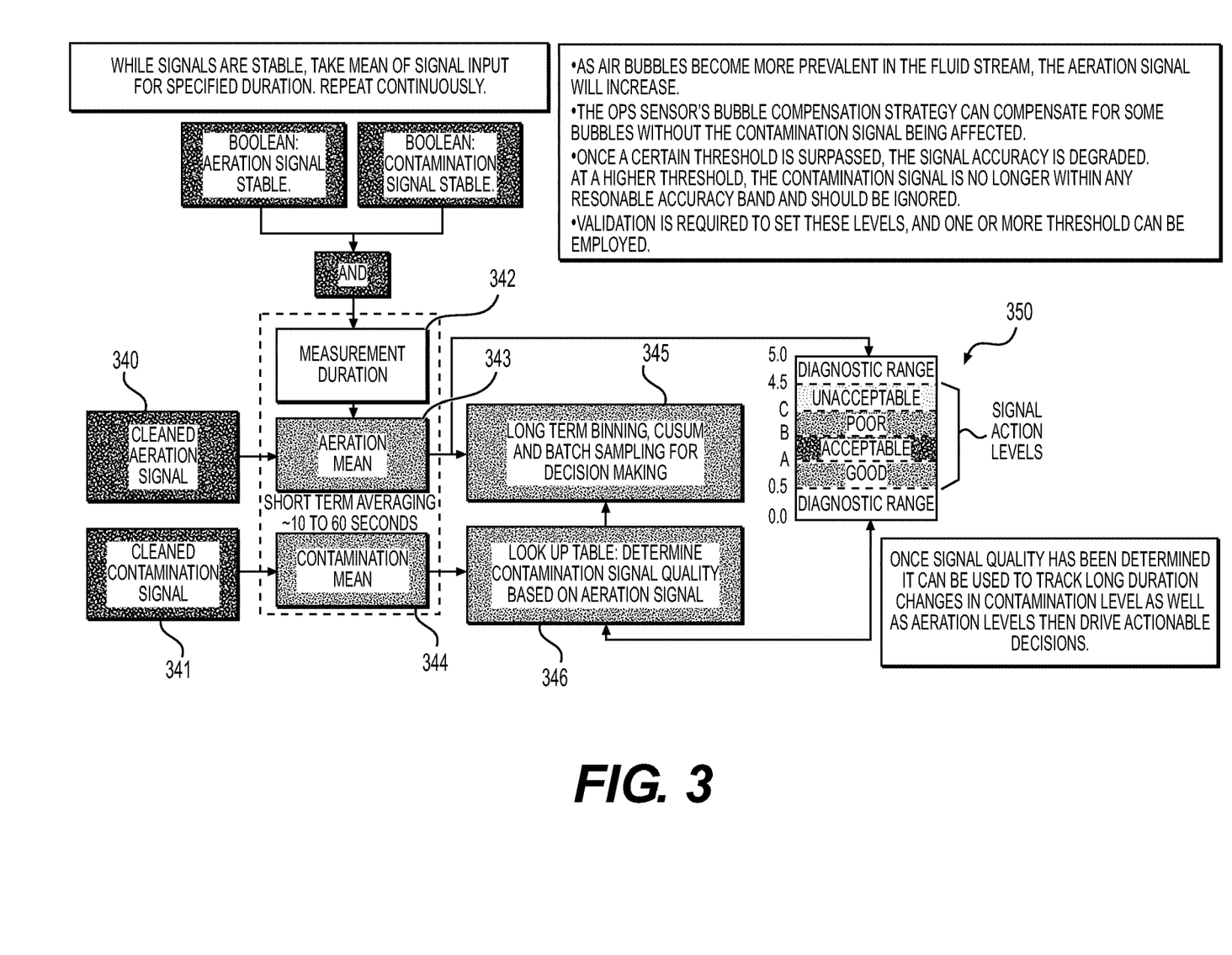
FIG. 3 illustrates an exemplary method for further processing signals received from the system of FIG. 2.

FIGS. 2 and 3 illustrate exemplary algorithms that may be implemented by the one or more processors 140 of external data processing system 110 before providing the cleaned and analyzed data derived from raw voltage outputs of optical particle sensor 115 to onboard monitoring and controlling module 150 of one or more machines. As shown in FIG. 2, an initial acceptable diagnostic range 210 (e.g., 0.45>V>4.75) for the raw voltage data received from photodiodes of optical particle sensor 115 may be predetermined in order to differentiate acceptable outputs from unacceptable outputs that may have resulted from an electrical short, one or more loose electrical connections, or other anomalies present somewhere in the system.

Aeration detection raw voltage data 132 and particle detection raw voltage data 134 may be separately processed according to the exemplary algorithm illustrated in FIG. 2, resulting in acceptable cleaned signals, shown as the output 240 of the algorithm in FIG. 2, and as cleaned aeration signal 340 and cleaned solid contaminate particle signal 341, shown as the input to the algorithm in FIG. 3. In the exemplary algorithm of FIG. 2, raw voltage data 132, 134 from optical particle sensor 115 may be monitored and averaged over time in accordance with a fast exponential weighted moving average 241 and a slow exponential weighted moving average 242. If desired, the results of slow exponential weighted moving average 242 may be utilized as a cleaned signal 243. Alternatively, and/or in addition, a difference 244 between the fast exponential weighted moving average 241 and the slow exponential weighted moving average 242 may be further analyzed in order to determine whether the difference is positive, indicative of a rising signal, and less than a rise rate threshold 245, or whether the difference is negative, indicative of a falling signal, and greater than a decay rate threshold 246. The processed voltage signals may also be selected in accordance with debounce times 247 and 248 that are designed to eliminate multiple fluctuating state transitions by reducing bouncing values for the voltage signals to a single, determinable value and preventing false trips. An acceptable cleaned signal 240 derived from each of the aeration detection raw voltage data 132 and particle detection raw voltage data 134 may then be provided in the form of a cleaned aeration signal 340 and a cleaned solid contaminate particle signal 341 to the further algorithm illustrated in FIG. 3.

As shown in FIG. 3, when both of cleaned aeration signal 340 and cleaned solid contaminate particle signal 341 are stable, cleaned aeration signal 340 and cleaned solid contaminate particle signal 341 may be analyzed over a measurement duration 342 to calculate an aeration mean value 343 and a solid contaminate particle mean value 344. In some exemplary implementations, aeration mean value 343 and solid contaminate particle mean value 344 may be determined over short term measurement durations of less than a minute. Alternative implementations may include other measurement durations. Multiple, successive aeration mean values 343 may then be grouped or binned 345 over longer durations, selectively subjected to further cumulative sum analysis (CUSUM), and batch sampling as desired under different operational circumstances and parameters before being provided to onboard monitoring and controlling module 150 for further decision making and application to control parameters to be implemented on a particular machine. Solid contaminate particle mean value 344 may be compared to a look-up table 346 to determine whether the signal quality is acceptable based on the observed aeration signal. An exemplary output 350 may include identification of whether the quality of output of a solid contaminate particle signal falls within a diagnostic range, and within one of a poor, acceptable, or good category for use in tracking long duration changes to solid contaminate particle levels as well as air bubble or aeration levels such that onboard monitoring and controlling module 150 can then assign different weights to the data.

A machine including machine system 100 and onboard monitoring and controlling module 150 may be a fixed or mobile machine configured to perform an operation associated with a particular industry, such as mining, construction, farming, etc. and operating between or within various project environments (e.g., construction sites, mine sites, power plants, etc.) A non-limiting example of a fixed machine system includes an engine system operating in a plant, a material conveyer, or off-shore environment (e.g., off-shore drilling platform). Non-limiting examples of mobile machines include commercial machines, such as trucks, cranes, earth moving vehicles, mining vehicles, backhoes, material handling equipment, farming equipment, marine vessels, aircraft, and any type of movable machine that operates in a work environment. A machine may be driven by a combustion engine, a fuel cell, an electric motor, or any combination thereof. The types of machines listed above are exemplary and not intended to be limiting.

Machine system 100 and external data processing system 110 of a machine implementing the features of this disclosure may also include or be operatively associated with on-board data collection and communication equipment to monitor, collect, and/or distribute information associated with one or more components of the machine. According to one embodiment, on-board data collection and communication equipment may include a system for early detection of failure of one or more components associated with the machine. It is contemplated that machine system 100 may include additional on-board data collection and communication equipment. For example, machine system 100 may include data monitoring equipment (e.g., sensors, control modules, data collectors, etc.) for monitoring health, productivity, status, and/or performance associated with a machine.

Machine system 100 may be configured to monitor one or more parameters associated with a fluid system of a machine. For example, machine system 100 may be implemented as part of a hydraulic system for generating and delivering hydraulic fluid to one or more hydraulically-actuated devices or actuators that control the movement of an implement or tool associated with a machine. Alternatively or additionally, machine system 100 may be implemented as part of a hydraulic transmission system that uses a pump/motor to operate the drive system for controlling the traction system of a machine.

Machine fluid systems may typically include a fluid channel that draws fluid from a reservoir. The fluid channel may deliver the fluid through a filtration device, which collects and removes particulate matter from the fluid. The fluid channel may then deliver the fluid to a pump, which compresses the fluid and facilitates circulation of the fluid within the fluid channel for eventual delivery to a load, such as an actuator for extending and retracting the boom, stick, or bucket on an excavator. The fluid channel may include any type of medium that may be configured to contain and direct the flow of fluid. For example, the fluid channel may include metallic, semi-metallic, alloy, rubber, polymer, and/or plastic pipes. The fluid channel may be used to connect a fluid source, such as contained in a reservoir, to one or more components that may operate on or otherwise utilize the fluid. The reservoir may include any type of tank for storing excess fluid that is not contained in the fluid channel or any components associated therewith. For example, the reservoir may include a storage tank adapted to store hydraulic fluid or other suitable fluid, or any other type of fluid for circulation through the fluid channel.

A filtration device may include any device for filtering, collecting, and storing contaminates, impurities, or other particulate matter from fluid flowing through the fluid channel. For example, a filtration device may include an oil filter, fuel filter, or any other type of filter suitable for removing contaminates from a fluid. A pump may be configured to produce a flow of pressurized fluid and may include a variable displacement pump, a fixed displacement pump, a variable flow pump, or any other device adapted to pressurize a fluid. The pump may be drivably connected to a power source by, for example, a countershaft, a belt, an electrical circuit, or in any other suitable manner. The pump may be dedicated to supplying pressurized fluid to a transmission, one or more hydraulic systems or components (e.g., work implements, etc.), an engine system, or other component associated with the fluid channel.

A load may be fluidly coupled to a pump and may embody any system that uses fluid pressurized by the pump to perform a task. For example, the load may include an implement coupled to the fluid channel of a hydraulic system. The implement may be configured to perform a task in response to the receipt of pressurized fluid from the pump. Excess fluid circulating through the load may be returned to the reservoir via the fluid channel. Machine fluid systems may also include one or more devices for controlling the operation of one or more components associated with the fluid systems. For example, a machine fluid system may include an electronic control module configured to control the operation of a pump, one or more valves, and/or a load. According to one embodiment, an electronic control module may be configured to provide one or more control signals for operating the pump in response to an operator instruction to move an implement associated with a machine.

Machine system 100 may include one or more components configured to monitor parameters associated with the fluid system and predict, based on the monitored parameters, failure of one or more components associated with the fluid system, or identify preventative actions that should be taken to avoid failures or suppress degradations in performance. System 100 may include, for example, one or more monitoring devices, such as optical particle sensor 115, and one or more pressure sensors, fluid flow sensors, temperature sensors, data collection devices, a communication network, and a condition monitoring system configured to provide data to a back office, one or more subscribers, or other end users of the data. Monitoring devices included within machine system 100 may include devices configured for accumulating performance data associated with one or more machines. For example, monitoring devices may include one or more sensors for measuring an operational parameter such as engine and/or machine speed, and machine pose and/or location; fluid pressure, flow rate, temperature, contamination level, and or viscosity of a fluid; electric current and/or voltage levels; fluid (i.e., fuel, oil, etc.) consumption rates; loading levels (i.e., payload value, percent of maximum payload limit, payload history, payload distribution, etc.); transmission output ratio, slip, etc.; haul grade and traction data; drive axle torque; intervals between scheduled or performed maintenance and/or repair operations; and any other operational parameter of the machines.

Optical particle sensor 115 may include any device configured to monitor and measure particle count data associated with a fluid flowing through a fluid channel. In various embodiments according to this disclosure, optical particle sensor 115 may be configured or modified to output raw voltage data representative of the amount of air bubbles or aeration in the fluid being tested and raw voltage data representative of the amount of solid contaminate particles in the fluid. Particle count data, as the term is used herein may include any data indicative of particles present in a fluid. For example, particle count data may include a number and size of particle present in a fluid flowing through a fluid chamber, an area occupied by a number of solid contaminate particles and/or air bubbles, the speed of the particles within the channel, the flow rate of fluid traveling through the fluid channel, or any other data that may be determined or derived from particles present in fluid flowing through the fluid channel. According to one exemplary embodiment, particle count data may include the International Organization for Standardization (ISO) 4406 method for the level of contamination by solid particles. In various exemplary embodiments of this disclosure, external data processing system 110 of machine system 100 may be configured to receive raw voltage data such as aeration detection raw voltage data 132 and particle detection raw voltage data 134 from internal photodiodes of optical particle sensor 115 rather than depending on any actual particle count output from the sensor for applications such as the fluid systems on heavy machinery where high levels of aeration in the hydraulic fluids may render the standard particle count outputs of optical particle sensor 115 unsatisfactory or unreliable.

A system and method according to various exemplary alternative embodiments and implementations of this disclosure may be configured for calibrating the standard output from a contaminant detection device, such as optical particle sensor 115, rather than processing the raw voltage data obtained from the sensor in the exemplary embodiments and implementations discussed above. As discussed above, optical particle sensor 115 is an example of a contaminant detection device configured to determine a level of contamination in a fluid. Various exemplary embodiments of optical particle sensor 115 may include an analog integrator configured to sum areas of shadows cast by contaminants in a fluid passing through a sensor passageway when a light emitting diode (LED) illuminates the fluid as it passes through the passageway, and a photodiode generates a voltage signal indicative of the area of each shadow. The analog integrator may be configured to integrate the resultant voltage signals over time, and output voltage signals that are correlated to the quantity of solid contaminate particles and air bubbles in the fluid. Nonetheless, optical particle sensor 115 may require calibration in order to have a high level of confidence in the particle count from the sensor when testing a fluid with high levels of air bubbles or aeration, such as the hydraulic fluids used in the hydraulic systems of heavy machinery.

An exemplary embodiment of a system for calibrating a contaminant detection device, such as an optical particle sensor, may include a test reservoir for holding a quantity of a fluid to be tested, a light-obscuration-type particle counter, and one or more of the contaminant detection devices fluidly connected in series to the test reservoir and the light-obscuration-type particle counter. Non-limiting examples of light-obscuration-type particle counters may include HIAC PODS+ portable liquid particle counter, Parker iCount online particle detector, ArgoHytos OPCount particle counter, and PAMAS S40 GO portable particle counter. In various exemplary embodiments, the test reservoir may be equipped with the light-obscuration-type particle counter. Alternatively, the light-obscuration-type particle counter may be provided separately from the test reservoir. The system may also include a filtration system configured to filter the fluid to be tested, such as a hydraulic fluid, to a baseline cleanliness level as reported by the contaminate detection device being tested and calibrated in the system.

Various exemplary implementations of a system for calibrating a contaminant detection device according to this disclosure may also include a low-end test dust dilution prepared from a first-sized test dust grade mixed with the fluid to create a first test dust mass-per-volume of the fluid. Test dust produced by controlled jet milling and/or sieving processes to meet test dust grades such as A.2 Fine, in accordance with International Organization for Standardization (ISO) 12103:2016 standards, may be obtained from sources such as Powder Technology Inc. (PTI). One or more intermediate test dust dilutions may also be prepared from the first-sized test dust grade mixed with the fluid to create a second test dust mass-per-volume of the fluid, wherein the second test dust mass-per-volume is greater than the first test dust mass-per-volume. In various alternative implementations, more than one intermediate test dust dilution may be prepared from the first-sized test dust grade. Additionally, a high-end test dust dilution may be prepared from the first-sized test dust grade mixed with the fluid to create a third test dust mass-per-volume of the fluid, wherein the third test dust mass-per-volume is greater than the second test dust mass-per-volume. In the alternative implementations that include more than one intermediate test dust dilutions, a set of second test dust masses-per-volume of the fluid may range in value between the first test dust mass-per-volume and the third test dust mass-per-volume.

An exemplary calibrating system according to this disclosure may still further include a pump configured to successively pump (or dose) each of the low-end, intermediate, and high-end test dust dilutions from the test reservoir through each of the one or more contaminant detection devices and the particle counter until a particle count measured by the particle counter for each of the successive test dust dilutions stabilizes and a voltage output from the contaminate detection device can be recorded. A first input mechanism may be configured for setting a low-end gain, an intermediate gain, and a high-end gain for each of the one or more contaminant detection devices based on the stabilized particle counts for each of the test dust dilutions using the first-sized test dust grade, as measured by the particle counter, and desired calibration curves for the contaminate detection devices.

The exemplary calibrating system according to this disclosure may also include an aeration bubble counter test dust dilution prepared from a second-sized test dust grade greater in size than the first-sized test dust grade and mixed with the fluid, wherein the second-sized test dust grade includes at least 90% of its volume containing dust particles falling within a range of sizes larger than a cut-off size (equivalent to an air bubble size threshold) associated with a voltage signal produced by one of the one or more contaminate detection devices indicative of the presence of an air bubble or aeration level contained within the fluid during use of the fluid in heavy machinery. The pump may be configured to pump the aeration bubble counter test dust dilution from the test reservoir through each of the one or more contaminant detection devices and the particle counter until a particle count measured by the particle counter for the aeration bubble counter test dust dilutions stabilizes. A second input mechanism may be configured for setting a bubble counting gain for each of the one or more contaminant detection devices such that each of the devices rejects approximately 70%-80% or more of the voltage signals generated as a result of the aeration bubble counter test dust dilution being pumped through the device.

The exemplary calibrating system may include three of the contaminate detection devices fluidly connected in series downstream of the test reservoir. The test reservoir in some exemplary embodiments of the calibrating system according to this disclosure may be a conical tank. The first-sized test dust grade may be ISO 12103-1:2016, A.2 fine test dust. A particle count of the low-end test dust dilution in one exemplary implementation may be approximately 160 counts per mL of the fluid, and a test dust mass of the low-end test dust dilution may be approximately 1.0 mg (milligram)/L (liter) of the fluid. The term "approximately" as used throughout this disclosure and in the claims will be understood by one of ordinary skill in the art to encompass a range of counts per mL and mass per volume, for example, that fall within standard industry tolerances for measuring particle counts and mass of test dust per volume of a fluid. A particle count of the intermediate test dust dilution in one exemplary implementation may be any one of approximately 640, 1,300, or 2,500 counts per mL of the fluid, respectively, and a test dust mass of the intermediate test dust dilution may be any one of approximately 0.414, 0.854, or 3.505 mg (milligram)/L (liter) of the fluid, respectively. A particle count of the high-end test dust dilution in one exemplary implementation may be approximately 5,000 counts per mL of the fluid, and a test dust mass of the high-end test dust dilution may be approximately 5.0 mg (milligrams)/L (liter) of the fluid. The second-sized test dust grade may be a test dust of a size in the range from approximately 75-150 microns in diameter. In an alternative implementation, the second-sized test dust grade may be a test dust of a size in the range from approximately 53-106 microns in diameter.

The above-described exemplary system for calibrating the standard output from a contaminant detection device, such as optical particle sensor 115, may be included as part of a system for early detection of potential operational issues on heavy machinery. Various embodiments of machine system 100 may include a data collector configured to receive, collect, package, and/or distribute data collected by optical particle sensor 115. For example, a data collector may receive particle count data from optical particle sensor 115, and calibrate the particle count data according to the above-described system and method. Alternatively and/or in addition, the data collector may acquire, analyze, and process raw voltage data produced by components of optical particle sensor 115, such as particle detection raw voltage data 134 and aeration detection raw voltage data 132, discussed above. The data collector of machine system 100 may package this data and transmit the received data to a condition monitoring system at a remote, back office or other recipient via a communication network. Alternatively and/or additionally, the data collector of machine system 100 may store the received data in memory for a predetermined time period, for later transmission to a condition monitoring system. For example, should a communication channel between machine system 100 and a remote condition monitoring system (e.g. a communication network or one or more communication devices associated with the data collector and/or the condition monitoring system) become temporarily unavailable, the collected data may be stored in memory for subsequent retrieval and transmission when the communication channel has been restored.

A communication network may include any network that provides two-way communication between a machine that includes machine system 100 and an off-board system (e.g., a condition monitoring system at a remote site). For example, a communication network may communicatively couple a machine to a condition monitoring system across a wireless networking platform such as, for example, a satellite communication system, a cellular communication system, or any other platform for communicating data with one or more geographically dispersed assets (e.g., Bluetooth, microwave, point-to-point wireless, point-to-multipoint wireless, multipoint-to-multipoint wireless.) Alternatively, a communication network may also include or embody any suitable wireless and/or wire-line networks such as, for example, Ethernet, fiber optic, waveguide, or any other type of wired communication network. It is also contemplated that communication network may support additional communication media or communication methods such as smart-card technology, manual data transport methods (sneakernet), or any suitable means for transporting data between a machine including machine system 100 and off-board systems. The communication network may also include any necessary infrastructure to support message routing and network operations, such as various hardware and software support systems and equipment that facilitates operations of one or more communication services.

A condition monitoring system that is part of or communicatively coupled with machine system 100 and processor 140 may include any type of processor-based system on which processes and methods consistent with the disclosed embodiments may be implemented. For example, the condition monitoring system may include one or more hardware and/or software components configured to execute software programs, such as software for monitoring and analyzing data associated with one or more machines. Machine system 100 may include one or more hardware components such as, for example, one or more processors 140, a random access memory (RAM) module, a read-only memory (ROM) module, a storage system, a database, one or more input/output (I/O) devices, and an interface. Alternatively and/or additionally, machine system 100 may include one or more software components such as, for example, a computer-readable medium including computer-executable instructions for performing methods consistent with certain disclosed embodiments. It is contemplated that one or more of the hardware components listed above may be implemented using software. For example, the storage for machine system 100 may include a software partition associated with one or more other hardware components.

Processor 140 may be configured to execute instructions and process data to perform one or more functions associated with machine system 100. Processor 140 may be communicatively coupled to RAM, ROM, storage, one or more databases, I/O devices, and an interface. Processor 140 may be configured to execute sequences of computer program instructions to perform various processes. The computer program instructions may be loaded into RAM for execution by processor 140. RAM and ROM may each include one or more devices for storing information associated with an operation of machine system 100, onboard monitoring and controlling module 150, and/or processor 140. For example, ROM may include a memory device configured to access and store information including information for identifying, initializing, and monitoring the operation of one or more components and subsystems of the machine. I/O devices may include one or more components configured to communicate information with a user associated with machine system 100, and to calibrate and make adjustments such as setting various gains on optical particle sensor 115 for different ranges of particle sizes to be detected and counted by the sensor. For example, I/O devices may include a console with an integrated keyboard and mouse to allow a user to input parameters associated with machine system 100 and optical particle sensor 115. I/O devices may also include a display including a graphical user interface (GUI) for outputting information on a monitor. I/O devices may also include peripheral devices such as, for example, a printer for printing information associated with machine system 100, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Processor 140 of machine system 100 may include one or more software applications for identifying trends in the amount of solid contaminate particles and air bubbles identified in fluids being tested, and prognosticating a future failure of a component associated with a machine fluid system. The software applications run by processor 140 may also be configured to notify one or more subscribers (e.g., repair personnel, project managers, dispatchers, etc.). For example, a software application associated with processor 140 may be configured to analyze historic and real time levels of contaminants such as the number and/or area of solid contaminant particles and air bubbles to estimate a trend in the particle count data. Processor 140 may compare current (e.g., real-time) particle count data with the historic trend data. If the current particle count data exceeds the historic particle count trend by a predetermined acceptable amount, processor 140 may trigger a failure event detection alarm, an indication that maintenance or repair is necessary, and/or generate an event notification for distribution to one or more subscribers.

A subscriber may include a computer system or mobile data device that is configured to receive data from processor 140 in a manner consistent with the disclosed embodiments. For example, a subscriber may include one or more computer terminals operated by respective users. Alternatively and/or additionally, a subscriber may include personal data assistant systems (PDA), wireless communication devices (e.g., pagers, phones, etc.), notebook computers, diagnostic computer systems, data analyzers, or any other such client computing devices configured to receive and process information. In one embodiment, a subscriber may be associated with one or more sections of a business entity associated with managing a remote project site within a project environment. For instance, a subscriber may be associated with a particular division of a business entity associated with a project environment, such as a project management division, an operations division, a maintenance and/or repair division, a procurement division, a human resource division, and/or any other business entity that may be associated with the project environment.

In another embodiment, a subscriber may be associated with a business entity that is affiliated with one or more sets of machines. For example, a subscriber may be associated with a site-manager that controls the operation and productivity of a first set of machines including machine system 100. Alternatively and/or additionally, different project entities may be associated with different business entities and/or machines. Accordingly, the above descriptions are exemplary and not intended to be limiting. The disclosed embodiments contemplate any correlation (or none at all) between one or more business entities, and/or sections thereof, and the components of a project environment.

A subscriber may be associated with a business entity affiliated with a particular project environment or work site and may be configured to communicate with one or more processors 140 of machine systems 100. In one embodiment, a subscriber may transmit and receive operation data to and from a processor 140 associated with one or more machines operating within a particular project environment. For example, a subscriber may be an on-site maintenance and repair division that receives component failure alerts (and/or particle count or pressure data associated with trends toward potential failures) associated with one or more machines from one or more processors 140.

A subscriber may also include portable communication devices associated with one or more personnel affiliated with a project environment or work site. For example, a subscriber may include a wireless pager or cell phone associated with a project manager, machine operator, dispatcher, repair technician, shift scheduler, or machine owner. As such, a subscriber may receive failure event warnings and alerts from a processor 140 and schedule the associated machine for inspection and/or repair before the predicted failure event occurs.

Processes and methods consistent with the disclosed embodiments provide a system for early detection of component failure associated with one or more components within a fluid flow path. More specifically, the system described herein provides a system for monitoring the trend of particle count data of fluid flowing in a fluid channel. If current data deviates from the monitored trend by a threshold amount, a potential future failure event may be identified and the machine may be flagged for investigation, testing, and/or repair. As an alternative or additional (i.e., redundant) embodiment, the system described herein may monitor the pressure at one or more locations along a fluid channel and identify a trend in the pressure data. If current pressure data deviates from the pressure trend, indicating a potential buildup of contaminates and debris associated with a component failure, the system may notify a subscriber to report the potential problem.

Processor 140 of machine system 100 may also be configured to utilize particle count data to schedule routine maintenance associated with the machine including machine system 100. For example, because some machines may be operated in harsher and/or more rigorous environments, each machine may require different maintenance schedules for hydraulic and/or other fluid systems. More particularly, engine and/or transmission lubrication and/or cooling systems associated with machines operating in harsh environments may require more frequent maintenance to counteract the increase of particulate matter caused by normal wear and tear than machines operating under less severe conditions. Accordingly, rather than prescribing periodic maintenance at set intervals, processor 140 may be adapted to determine when wear debris has reached a level that requires system maintenance.

While nominal increases in particle count trends are indicative of normal "wear-and-tear", dramatic deviations from these trends may be indicative of a material failure of one or more components in the system. Accordingly, as processor 140 receives current ("real-time" or near-"real-time") particle count data from different machines, one or more processors 140 of various machine systems 100 may compare the current data with the historic particle count trend. If the current particle count data does not deviate from the historic part count trend by a threshold amount, processor 140 may continue monitoring the current particle count data.

The threshold level for characterizing deviations in current particle count data with respect to historic particle count data may be predetermined based, for example, on empirical test data gathered during failure test analysis associated with components of the fluid system. Alternatively, the threshold level may be established by estimating the increase in particulate expulsion associated with certain "minor" failure events that may occur prior to complete component failure. For example, pump impeller bearings may begin to break down some time before total failure of the pump. Consequently, when the impeller bearings being to deteriorate particulate debris may be expelled into a fluid channel. As the pump impeller condition gradually declines, additional material may be introduced into the fluid. These initial "warning signs" may be observed as uncharacteristic increases in particle count in additional to the normal "wear-and-tear" particle count data. Thus, the threshold level for an acceptable increase in historic particle count data may be established as a predetermined percentage above the historical increase. Accordingly, if the historical trend indicates that, for every 10 hours of engine operation, particle count data has increased 1½%-2½%, the threshold for characterizing a deviation in current data from historical trend data may be established as, for example, 4%.

It is contemplated that additional and/or different methods may be used for determining an acceptable threshold for identifying failure event based on particle count data. For example, if, during monitoring of a machine during a catastrophic failure event, the particle count data increased by 10% over the historical trend, the threshold level may be set as some level less than 10%. Those skilled in the art will recognize that the lower this level is set, the earlier that a failure event prediction is made, which may also increase the number of false component failure predictions.

If the current particle count data deviates from the historic particle count trend by a threshold amount, processor 140 of machine system 100 may predict a component failure event. Because components often fail very quickly from the onset of certain failure symptoms, processor 140 may be configured to immediately generate an event notification through onboard monitoring and controlling module 150. This event notification may include an audible and/or visual alarm within the cab of the machine, advising the driver of a potential component failure condition.

In addition to generating an on-board machine alarm, processor 140 and/or onboard monitoring and controlling module 150 may also be configured to generate an electronic message, such as a text message, e-mail message, page, short-message-service (SMS) message, automated voice message, a voicemail message, or any other suitable electronic message. Processor 140 and onboard monitoring and controlling module 150 may transmit this message to one or more subscribers. As a result, the subscribers may be able to take appropriate action to reduce the impact of a component failure. For example, a project manager or dispatcher may schedule immediate maintenance with a repair facility and schedule a replacement rental machine to prevent a lapse in productivity during the repair(s).

Optionally, upon predicting a catastrophic failure associated with the machine, processor 140 and onboard monitoring and controlling module 150 may generate a control signal to shut down the machine before the occurrence of the failure event. This may be particularly advantageous in a fluid system where failure of one component may result in significant collateral damage to the machine or one or more critical components associated therewith. For example, if processor 140 predicts a component failure associated with the fluid cooling system for an engine, processor 140 may generate a command signal to shut down the engine to prevent overheating of the engine and damage associated therewith.

INDUSTRIAL APPLICABILITY

Systems and methods consistent with the disclosed embodiments provide a solution for obtaining accurate and reliable particle counts using raw voltage data correlated with the number of solid contaminate particles and air bubbles in a fluid being tested in order to provide early detection of trends that may lead to failure or required maintenance of components associated with machine fluid systems. Machines that employ the presently disclosed systems and associated methods may be configured to detect and monitor the number and size of solid contaminate particles and air bubbles or aeration present in fluid flowing through a fluid channel. The systems and methods described herein may also detect trends in the levels of contaminates in various fluids such as hydraulic fluid used in heavy machinery, and prognosticate potential future failures or maintenance intervals for one or more components of a machine that are affected by the fluid. As a result, work environments that implement the presently disclosed system for early detection of machine component failure may enable project managers, machine operators, and equipment owners to preemptively identify and repair damaged components before catastrophic component failure that may disable the machine and have a significant impact on the productivity of the work environment.

Figure 4:
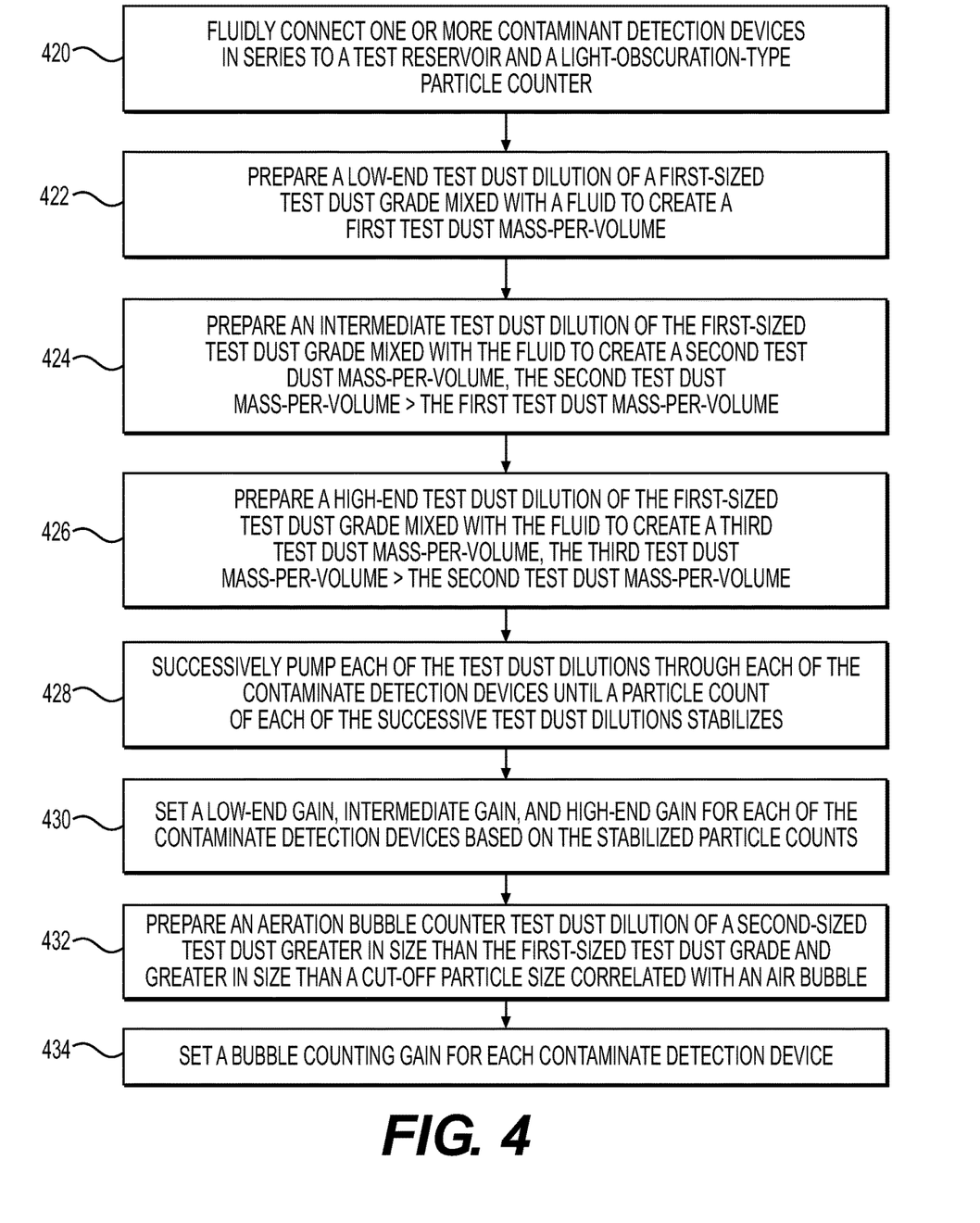
FIG. 4 provides a flowchart depicting an exemplary method for calibrating the output from the optical particle sensor of FIG. 1.

FIG. 4 illustrates one exemplary implementation of a method for calibrating an optical particle sensor or other contaminate detection device according to various embodiments of this disclosure. As shown in FIG. 4, one or more contaminate detection devices 115 may be fluidly connected in series to a test reservoir and a light-obscuration-type particle counter at Step 420. A low-end test dust dilution may be prepared from a first-sized test dust grade mixed with a fluid to create a first test dust mass-per volume at Step 422. An intermediate test dust dilution may be prepared from the first-sized test dust grade mixed with the fluid to create a second test dust mass-per-volume, wherein the second test dust mass-per-volume is greater than the first test dust mass-per-volume at Step 424. A high-end test dust dilution may also be prepared from the first-sized test dust grade mixed with the fluid to create a third test dust mass-per-volume, wherein the third test dust mass-per-volume is greater than the second test dust mass-per-volume at Step 426.

After preparation of each of the test dust dilutions described above, each test dust dilution may be successively pumped through each of the contaminate detection devices that are fluidly connected in series to the test reservoir until a particle count of each of the test dust dilutions stabilizes at Step 428. After stabilization of each of the particle counts for each of the test dust dilutions, an input device may be used to set a low-end gain, an intermediate gain, and a high-end gain for each of the contaminant detection devices based on the stabilized particle counts at Step 430.

In order to calibrate the contaminate detection devices such that unacceptable errors in particle count caused by the presence of air bubbles are eliminated or suppressed, at Step 432 an aeration bubble counter test dust dilution may also be prepared from a second-sized test dust grade that is greater in size than the first-sized test dust grade and containing a majority volume percent of test dust particle sizes greater in size than a cut-off particle size correlated with an air bubble. At Step 434, the input device may be used to set a bubble counting gain for each contaminate detection device such that each contaminate detection device, such as optical particle sensor 115, rejects all counts of particles larger than the cut-off particle size as air bubbles.

Although the disclosed embodiments are described and illustrated as being associated with fluid systems for heavy machinery, they may be implemented in any mobile or stationary machine comprising at least one fluid delivery system. Specifically, the presently disclosed systems and methods for calibrating a contaminate detection device, or for analyzing and processing raw voltage data produced by the contaminate detection device indicative of the number or area of solid contaminate particles and air bubbles may enhance early detection of machine component failures. The disclosed systems and methods may be used in any machine or equipment system where it may be advantageous to monitor the amount of contaminates or debris in a fluid, particularly in systems where circulation of debris or high levels of contaminates or air bubbles may potentially damage components of the machine or restrict the flow of fluid necessary to ensure proper operation of the machine. Furthermore, the presently disclosed systems and associated methods may be integrated with a connected worksite environment that monitors, analyzes, and manages operations of a plurality of machines to ensure efficient operation of the worksite.

The presently disclosed systems and methods for early detection of machine component failure may have several advantages. For example, the presently disclosed systems employ a contaminate detection device that directly monitors the area of solid contaminate particles and air bubbles present in the fluid, which directly detects the presence of failure debris or amounts of contaminates indicative of imminent failure of a component. In contrast, conventional systems use indirect methods for detecting failure debris (e.g., by monitoring pressure drop across a fluid filter). However, such indirect methods may not immediately respond to increases in failure debris (e.g., until the fluid filter becomes clogged), potentially delaying the detection of a failure condition, which may result in further damage to the machine.

It will be apparent to those skilled in the art that various modifications and variations can be made to the disclosed systems and methods without departing from the scope of the disclosure. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A method for calibrating a contaminant detection device configured to determine a level of contamination in a fluid using an analog integrator that sums areas of shadows cast by contaminants in a fluid passing through a passageway when a light emitting diode (LED) is used to illuminate the fluid and a photodiode is used to generate a voltage signal indicative of the area of each shadow, with the analog integrator integrating the resultant voltage signals over time, the method comprising:

fluidly connecting one or more of the contaminant detection devices in series to a test reservoir and to a light-obscuration-type particle counter;

preparing a low-end test dust dilution of a first-sized test dust grade mixed with the fluid to create a first test dust mass-per-volume of the fluid;

preparing an intermediate test dust dilution of the first-sized test dust grade mixed with the fluid to create a second test dust mass-per-volume of the fluid, the second test dust mass-per-volume being greater than the first test dust mass-per-volume;

preparing a high-end test dust dilution of the first-sized test dust grade mixed with the fluid to create a third test dust mass-per-volume of the fluid, the third test dust mass-per-volume being greater than the second test dust mass-per-volume;

successively pouring each of the low-end, intermediate, and high-end test dust dilutions into the test reservoir and pumping each of the test dust dilutions through each of the one or more contaminant detection devices and the particle counter until a particle count measured by the particle counter for each of the successive test dust dilutions stabilizes;

setting a low-end gain, an intermediate gain, and a high-end gain for each of the one or more contaminant detection devices based on the stabilized particle counts for each of the test dust dilutions using the first-sized test dust grade;

preparing an aeration bubble counter test dust dilution of a second-sized test dust grade greater in size than the first-sized test dust grade and mixed with the fluid, wherein the second-sized test dust grade comprises at least 90% of its volume containing dust particles falling within a range of sizes larger than a predetermined cut-off particle size associated with a voltage signal produced by one of the one or more contaminate detection devices and indicative of the presence of an air bubble contained within the fluid during use of the fluid in heavy machinery;

pouring the aeration bubble counter test dust dilution into the test reservoir and pumping the aeration bubble counter test dust dilution through each of the one or more contaminant detection devices and the particle counter until a particle count measured by the particle counter for the aeration bubble counter test dust dilutions stabilizes; and setting a bubble counting gain of an aeration threshold for each of the one or more contaminant detection devices such that each of the devices rejects approximately 70-80% or more of the voltage signals generated as a result of the aeration bubble counter test dust dilution being pumped through the device.

2. The method of claim 1, wherein three of the contaminate detection devices are fluidly connected in series downstream of the test reservoir.

3. The method of claim 1, wherein the test reservoir is a conical tank.

4. The method of claim 1, wherein the first-sized test dust grade comprises International Organization for Standardization (ISO) 12103-1:2016, A.2 fine test dust.

5. The method of claim 1, wherein a particle count of the low-end test dust dilution is approximately 160 counts per mL of the fluid, and a test dust mass of the low-end test dust dilution is approximately 1.0 mg (milligram)/L (liter) of the fluid.

6. The method of claim 1, wherein a particle count of the intermediate test dust dilution is any one of approximately 640, 1,300, or 2,500 counts per mL of the fluid, respectively, and a test dust mass of the intermediate test dust dilution is any one of approximately 0.414, 0.854, or 3.505 mg (milligram)/L (liter) of the fluid, respectively.

7. The method of claim 6, wherein a particle count of the high-end test dust dilution is approximately 5,000 counts per mL of the fluid, and a test dust mass of the high-end test dust dilution is approximately 5.0 mg (milligrams)/L (liter) of the fluid.

8. The method of claim 1, wherein the second-sized test dust grade comprises test dust of a size in the range from approximately 75-150 microns in diameter.

9. The method of claim 1, wherein the second-sized test dust grade comprises test dust of a size in the range from approximately 53-106 microns in diameter.

10. A system configured for calibrating a contaminant detection device, wherein the contaminant detection device determines a level of contamination in a fluid using an analog integrator that sums areas of shadows cast by contaminants in a fluid passing through a passageway when a light emitting diode (LED) illuminates the fluid as it passes through the passageway, and a photodiode generates a voltage signal indicative of the area of each shadow, with the analog integrator integrating the resultant voltage signals over time, the system comprising:
 a test reservoir;
 a light-obscuration-type particle counter;
 one or more of the contaminant detection devices fluidly connected in series to the test reservoir and the light-obscuration-type particle counter;
 a low-end test dust dilution prepared from a first-sized test dust grade mixed with the fluid to create a first test dust mass-per-volume of the fluid;
 an intermediate test dust dilution prepared from the first-sized test dust grade mixed with the fluid to create a second test dust mass-per-volume of the fluid, the second test dust mass-per-volume being greater than the first test dust mass-per-volume;
 a high-end test dust dilution prepared from the first-sized test dust grade mixed with the fluid to create a third test dust mass-per-volume of the fluid, the third test dust mass-per-volume being greater than the second test dust mass-per-volume;
 a pump configured to successively pump each of the low-end, intermediate, and high-end test dust dilutions from the test reservoir through each of the one or more contaminant detection devices and the particle counter until a particle count measured by the particle counter for each of the successive test dust dilutions stabilizes;
 a first input mechanism for setting a low-end gain, an intermediate gain, and a high-end gain for each of the one or more contaminant detection devices based on the stabilized particle counts for each of the test dust dilutions using the first-sized test dust grade;
 an aeration bubble counter test dust dilution prepared from a second-sized test dust grade greater in size than the first-sized test dust grade and mixed with the fluid, wherein the second-sized test dust grade comprises at least 90% of its volume containing dust particles falling within a range of sizes larger than a cut-off size associated with a voltage signal produced by one of the one or more contaminate detection devices indicative of the presence of an air bubble contained within the fluid during use of the fluid in heavy machinery;
 a pump configured to pump the aeration bubble counter test dust dilution from the test reservoir through each of the one or more contaminant detection devices and the particle counter until a particle count measured by the particle counter for the aeration bubble counter test dust dilutions stabilizes; and
 a second input mechanism for setting a bubble counting gain for each of the one or more contaminant detection devices such that each of the devices rejects approximately 70-80% or more of the voltage signals generated as a result of the aeration bubble counter test dust dilution being pumped through the device.

11. The system of claim 10, wherein three of the contaminate detection devices are fluidly connected in series downstream of the test reservoir.

12. The system of claim 10, wherein the test reservoir is a conical tank.

13. The system of claim 10, wherein the first-sized test dust grade comprises International Organization for Standardization (ISO) 12103-1:2016, A.2 fine test dust.

14. The system of claim 10, wherein a particle count of the low-end test dust dilution is approximately 160 counts per mL of the fluid, and a test dust mass of the low-end test dust dilution is approximately 1.0 mg (milligram)/L (liter) of the fluid.

15. The system of claim 10, wherein a particle count of the intermediate test dust dilution is any one of approximately 640, 1,300, or 2,500 counts per mL of the fluid, respectively, and a test dust mass of the intermediate test dust dilution is any one of approximately 0.414, 0.854, or 3.505 mg (milligram)/L (liter) of the fluid, respectively.

16. The system of claim 15, wherein a particle count of the high-end test dust dilution is approximately 5,000 counts per mL of the fluid, and a test dust mass of the high-end test dust dilution is approximately 5.0 mg (milligrams)/L (liter) of the fluid.

17. The system of claim 10, wherein the second-sized test dust grade comprises test dust of a size in the range from approximately 75-150 microns in diameter.

18. The system of claim 10, wherein the second-sized test dust grade comprises test dust of a size in the range from approximately 53-106 microns in diameter.

19. A system for early detection of potential operational issues on heavy machinery, the system comprising:
 a hydraulic fluid contaminant detection device, wherein the contaminant detection device determines a level of contamination in a hydraulic fluid used in the heavy machinery by using an analog integrator that sums areas of shadows cast by contaminants in the hydraulic fluid passing through a passageway when a light emitting diode (LED) illuminates the hydraulic fluid as it passes through the passageway, and a photodiode generates a voltage signal indicative of the area of each shadow, with the analog integrator integrating the resultant voltage signals over time;
 a test reservoir fluidly connected to the hydraulic fluid contamination detection device;
 a light-obscuration-type particle counter fluidly connected downstream of the hydraulic fluid contamination detection device;
 a low-end test dust dilution prepared from a first-sized test dust grade mixed with the hydraulic fluid to create a first test dust mass-per-volume of the hydraulic fluid;
 an intermediate test dust dilution prepared from the first-sized test dust grade mixed with the hydraulic fluid to create a second test dust mass-per-volume of the hydraulic fluid, the second test dust mass-per-volume being greater than the first test dust mass-per-volume;
 a high-end test dust dilution prepared from the first-sized test dust grade mixed with the hydraulic fluid to create a third test dust mass-per-volume of the hydraulic fluid, the third test dust mass-per-volume being greater than the second test dust mass-per-volume;
 a pump configured to successively pump each of the low-end, intermediate, and high-end test dust dilutions from the test reservoir through the hydraulic fluid contaminant detection device and the particle counter until a particle count measured by the particle counter for each of the successive test dust dilutions stabilizes;

a first input mechanism for setting a low-end gain, an intermediate gain, and a high-end gain for the hydraulic fluid contaminant detection device based on the stabilized particle counts for each of the test dust dilutions using the first-sized test dust grade;

an aeration bubble counter test dust dilution prepared from a second-sized test dust grade greater in size than the first-sized test dust grade and mixed with the hydraulic fluid, wherein the second-sized test dust grade comprises at least 90% of its volume containing dust particles falling within a range of sizes larger than a cut-off size associated with a voltage signal produced by one of the hydraulic fluid contaminate detection device indicative of the presence of an air bubble contained within the hydraulic fluid during use of the hydraulic fluid in the heavy machinery;

the pump being further configured to pump the aeration bubble counter test dust dilution from the test reservoir through the hydraulic fluid contaminant detection device and the particle counter until a particle count measured by the particle counter for the aeration bubble counter test dust dilution stabilizes; and a second input mechanism for setting a bubble counting gain for the hydraulic fluid contaminant detection device such that the device rejects approximately 70-80% or more of the voltage signals generated as a result of the aeration bubble counter test dust dilution being pumped through the device.

20. The system of claim 19, wherein:

a particle count of the low-end test dust dilution is approximately 160 counts per mL of the fluid, and a test dust mass of the low-end test dust dilution is approximately 1.0 mg (milligram)/L (liter) of the fluid;

a particle count of the intermediate test dust dilution is any one of approximately 640, 1,300, or 2,500 counts per mL of the fluid, respectively, and a test dust mass of the intermediate test dust dilution is any one of approximately 0.414, 0.854, or 3.505 mg (milligram)/L (liter) of the fluid, respectively; and a particle count of the high-end test dust dilution is approximately 5,000 counts per mL of the fluid, and a test dust mass of the high-end test dust dilution is approximately 5.0 mg (milligrams)/L (liter) of the fluid.

* * * * *